United States Patent [19]

Gysling

[11] 4,287,354
[45] Sep. 1, 1981

[54] TELLURIUM(II) COMPOUNDS AND COMPLEXES HAVING ORGANIC MOIETIES CONTAINING SILICON

[75] Inventor: Henry J. Gysling, Rochester, N.Y.

[73] Assignee: Eastman Kodak Company, Rochester, N.Y.

[21] Appl. No.: 198,690

[22] Filed: Oct. 20, 1980

Related U.S. Application Data

[62] Division of Ser. No. 965,712, Dec. 1, 1978, Pat. No. 4,258,128.

[51] Int. Cl.$^3$ .............................................. C07F 7/08
[52] U.S. Cl. .................................. 556/465; 556/489; 548/110; 260/429 J; 260/429 R; 260/430; 260/438.1; 260/439 R
[58] Field of Search ................. 556/465, 489; 548/110

[56] References Cited

U.S. PATENT DOCUMENTS

3,763,197  10/1973  Collier et al.
4,187,240  2/1980   Gardner et al. ................ 556/465 X

OTHER PUBLICATIONS

K. J. Irgolic, The Organic Chemistry of Tellurium, Gordon and Breach Science, Publ., London, 1974.
K. J. Irgolic, J. Organometal. Chem. 103, 91, 1975, pp.123-125 and 140-147.

*Primary Examiner*—Paul F. Shaver
*Attorney, Agent, or Firm*—John R. Everett

[57] ABSTRACT

Nonpolar, organic solvent-soluble tellurium compounds and complexes are disclosed. The compounds are tellurium(II) compounds and are represented by the formula:

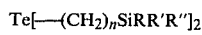

Te[—(CH$_2$)$_n$SiRR'R"]$_2$ wherein:
n is an integer from 1 to 10 and
R, R' and R" are independently selected from the group consisting of alkyl, aryl and heterocyclic radicals. Photosensitive complexes of these compounds with transition metals, as well as photographic elements having layers comprising these complexes, are also disclosed.

6 Claims, No Drawings

TELLURIUM(II) COMPOUNDS AND COMPLEXES HAVING ORGANIC MOIETIES CONTAINING SILICON

This is a division of application Ser. No. 965,712 filed Dec. 1, 1978, now U.S. Pat. No. 4,258,128.

BACKGROUND OF THE INVENTION

1. Field of the Invention

The present invention relates to diorganotellurium-(II) compounds and complexes. More particularly, it relates to diorganotellurium(II) compounds wherein the organic radical contains silicon. The described diorganotellurides and transition metal coordination complexes incorporating these diorganotellurides as ligands are soluble in nonpolar organic solvents, making them particularly useful in various catalytic processes including catalytic imaging processes.

2. Description Relative to the Prior Art

Diorganotellurium compounds are well-known in the art. Organic radicals which are bonded to a tellurium-(II) or a tellurium(IV) atom can take a wide variety of forms. For example, diorganotellurium dihalides and dicarboxylates are know. (See K. J. Irgolic, *The Organic Chemistry of Tellurium*, Gordon and Breach Science, Publ., London, 1974.) These diorganotellurium compounds have been found to be useful as oxidants in tellurium physical development processes. It is also known that certain diorganotellurium compounds can function as ligands for certain transition metal compounds. For example, complexes such as $Cu_2Br_2[Te(C_6H_5)_2]_4$, $CuI[TE(p-MeC_6H_4)_2]$ and the like are known. These prior-art complexes have no significant nonpolar organic solvent solubility. This is unfortunate because solubility in these solvents would offer many advantages where the complex is used as the oxidant in an image-forming combination or is part of the light-sensitive component in a photographic element.

Certain silicon-containing moieties can impart nonpolar organic solvent solubility to certain organometallic compounds. This is taught, for example, by Collier et al, U.S. Pat. No. 3,763,197. Thus, compounds such as $Ti[CH_2Si(CH_3)_3]_4$ and the like are known to have useful nonpolar organic solvent solubility. While it may appear desirable to form similar tellurium compounds, difficulties would be encountered if this were attempted. Known organometallic compounds having these silicon-containing moieties are made using a conventional salt-elimination reaction, i.e., using a Grignard reagent. If a similar preparation were attempted with tellurium as the metal, only the tellurium(IV) compound would be produced, e.g., $TE-CH_2Si(CH_3)_3]_2Cl_2$. The prior art suggests no method of making stable, nonpolar, organic solvent-soluble tellurium(II) compounds with these silicon-containing moieties.

SUMMARY OF THE INVENTION

It has been found according to the present invention that certain diorganotellurium(II) compounds can be made, which compounds have high solubility in nonpolar organic solvents. The new diorganotellurides of the present invention are stable tellurium(II) compounds and can be represented by the formula:

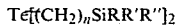

wherein:

n is an integer from 1 to 10 and

R, R' and R" are independently selected from the group consisting of alkyl, aryl and heterocyclic radicals.

Not only do the compounds described above have high solubility in nonpolar organic solvents, but transition metal complexes of these compounds retain this solubility. Thus, in another aspect of the present invention there are provided transition metal complexes of the described tellurium(II) compounds. Useful complexes can be made, for example, from silver copper, palladium, manganese and cobalt. Particularly useful complexes are those having the general formulae:

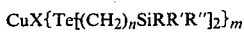

and

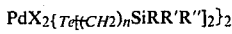

wherein:

X is a halogen or a pseudohalogen, m is an integer from 1 to 3 and n, R, R' and R" are as described above.

The tellurium(II) compounds of the present invention can be used as the source of tellurium in a physical development process. Thus, in another aspect of the present invention there is provided an image-forming combination comprising (i) the described tellurium(II) compound and (ii) a reducing agent. The image-forming combination can be coated, either with or without a binder, on a suitable support to form a useful amplification element. The image-forming combination can also be in a solution which is useful as a tellurium physical development bath.

The silver, copper and palladium transition metal complexes described above are light-sensitive. Thus, in another aspect of the present invention there is provided a photographic element comprising a support and having coated thereon a layer comprising the transition metal complex described above.

The compounds described above are liquids which can be converted to solids by oxidation with halogens to yield the tellurium(IV) derivative, for example, $I_2Te[CH_2Si(CH_3)_3]_2$. The described tellurium(IV) solids are also highly soluble in nonpolar organic solvents. Thus, the silicon-containing moieties impart the desired solubility to the tellurium compound or complex of which it is a part. As a result, the present invention provides a ready source of soluble transition metal catalyst. Further, for the first time it is possible to coat transition metal complexes such as copper and palladium light-sensitive complexes from inexpensive and readily available nonpolar solvents.

DETAILED DESCRIPTION OF THE INVENTION

The new tellurium(II) compound (1) and the preferred complexes (2) and (3) of the present invention can be represented by the formulae:

 (1)

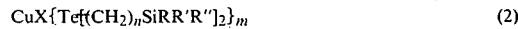 (2)

and

 (3)

The integer n can be from 1 to 10, and the integer m is from 1 to 3. While alkylene chains longer than 10 carbon atoms are useful for some purposes, compounds having shorter alkylene chains tend to be more soluble in nonpolar organic solvents. Thus, a lower alkylene, i.e., when n is from 1 to 4, is preferred, particularly when n is equal to 1. Similarly, while R, R' and R" can be either alkyl having, for example, 1 to 10 carbon atoms such as methyl, ethyl, isopropyl or aryl such as phenyl including substituted aryl or multiple ring aromatic groups such as napthyl, smaller groups such as phenyl are preferred because they tend to increase solubility. R, R' and R" can also be heterocyclic groups. Useful heterocyclic radicals include thiazoles, isoxazoles, benzothiazoles, benzoxazoles, phenyloxazoles and the like. Again, smaller groups are preferred. At least two of R, R' and R" are preferably lower alkyl, particularly methyl. The anion X in the copper and palladium complexes described above can be halogen such as chlorine, bromine and iodine or a pseudohalogen. Pseudohalogens are anions which have properties very similar to halogens such as $SCN^-$, $NCO^-$, $NCSe^-$, $NCTe^-$ and the like. In the copper complexes, m can be an integer from 1 to 3. The exact value of m depends on the coordination number assumed by the copper atom of the complex.

Illustrative compounds and complexes according to the present invention include:

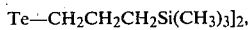

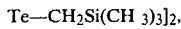

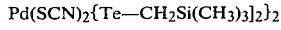
and

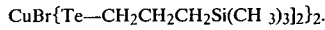

The described diorganotellurium(II) compounds and their transition metal complexes are soluble in nonpolar organic solvents. By "soluble" is meant that it is possible to form at least a 0.1 M solution of the tellurium(II) compound or complex in the selected solvent at room temperature. Typically, however, the preferred compounds are more soluble and 1.0 M solutions of the compounds are possible in nonpolar organic solvents at room temperature. Typical nonpolar organic solvents include ethers such as dimethyl ether, diethyl ether and the like; saturated hydrocarbons including hexane, cyclohexane; and other common organic solvents.

The new diorganotellurium(II) compounds of the present invention can be prepared by a two-step reaction sequence. In the first step, elemental tellurium is reduced to tellurium (2−). This can be accomplished, for example, by reacting tellurium metal with a reducing agent such as potassium borohydride in an aqueous solution of sodium hydroxide. In the second step, the tellurium (2−) is reacted with two equivalents of the appropriate silicon-containing alkyl halide in an alcohol solution. Because the tellurium (2−) is extremely airsensitive, these steps should be carried out in an inert atmosphere such as nitrogen or argon. After refluxing the tellurium (2−) and silicon-containing alkyl halide solution for a time sufficient to complete the reaction, typically 3—20 hours, the alcohol is distilled from the solution. The diorganotellurium(II) is then extracted from the aqueous solution with a suitable solvent such as ethyl ether. The resulting diorganotellurium(II) is a liquid at room temperature and can be purified by conventional methods such as by vacuum distillation. Alkyl halides containing the necessary tertiary silicon atom are known in the art. Examples of useful silicon-containing alkyl halides include $(CH_3)_3SiCH_2CH_2CH_2Cl$, $C_6H_5(CH_3)_2SiCH_2Cl$, $[(CH_3)_3-Si]_2CHCl$, $(C_2H_5)_3SiCH_2Cl$ and the like.

The transition metal complexes of the diorganotellurium(II) compounds of the present invention can be prepared by known methods. Useful methods are described, for example, in U.S. Pat. No. 3,859,092 and by M. R. Collier et al, *J. Chem. Soc.* (Dalton), 445 (1973). For example, copper(I) diorganotellurium(II) complexes can be prepared by reacting the proper copper(I) halide with a diorganotellurium(II) compound of the invention in a solution of chloroform or methylene chloride. Palladium complexes of the diorganotellurium(II) compounds of the present invention are conveniently prepared by a substitution reaction by using the appropriate palladium complex which is coordinated to labile ligands. Useful palladium complexes for this substitution reaction include $K_2Pd(SCN)_4$, $K_2PdCl_4$, $K_2Pd(C_2O_4)_4$ and $PdCl_2(NCC_6H_5)_2$.

A preferred embodiment of the present invention is an image-forming combination comprising (i) the described tellurium(II) compound or complex as an oxidizing agent and (ii) a reducing agent. The image-forming combination can be in a solvent, which can be a nonpolar organic solvent, thereby forming a physical developer solution. Alternatively, the image-forming combination can be on a suitable support either alone or with other components including light-sensitive components, other oxidants, binders and the like. Suitable methods of making and using the present image-forming combination can be found in copending, commonly assigned U.S. Applications Ser. Nos. 848,062 and 848,063 filed Nov. 3, 1977. Because of their desirable solubility properties, the image-forming combination of the present invention can be used with, and coated from, nonpolar organic solvents. Suitable solvents of this type are described above in relation to the solubility of the present compounds.

Because the transition metal complexes described above are light-sensitive, they can be coated, using nonpolar organic solvents, onto or imbibed into suitable photographic supports to provide useful photographic elements. The complexes can be used individually or mixtures of two or more of the complexes can be used. A photosensitive element can be prepared by soaking porous paper in a solution containing the transition metal complex of the diorganotellurium(II) compound of the present invention. The paper is then dried, thereby producing a photosensitive element. If desired, the compound can be added to a binder solution and coated onto a substrate by any means, such as dip coating, brushing, rolling, spraying, hopper coating or the like.

The binder used as a vehicle for the photosensitive complex can be any of the hydrophilic binders used in photographic elements, including natural materials such as gelatin, albumin, agar-agar, gum arabic, alginic acid, etc., and synthetic materials such as poly(vinyl alcohol), poly(vinyl pyrrolidone), cellulose esters, partially hydrolyzed cellulose acetate and the like. Because the complexes are soluble in nonpolar organic solvents, polymers which are soluble in these solvents can be used as binders. Typical binders of this type include polystyrene, poly(vinyl butyral) and cellulose acetate butyrate. It is noted that, although many binders may be used herein, the binder should be permeable to the developer used if a solution is used to process the element. The binder should not absorb appreciably in the region of sensitivity of the compound. The compound may be used with varying amounts of binder material. Preferably, the compound-to-binder weight ratio is from about 3:1 to about 1:2.

The complex can be either imbibed into or coated onto any support typically used for photographic elements. Support materials used herein are subject to wide variation. Glass can be used as can be metals such as aluminum, copper, zinc and tin. Conventional film bases such as cellulose acetate, cellulose nitrate, cellulose acetate butyrate, poly(ethylene terephthalate), polystyrene and paper, including polyethylene-coated paper and polypropylene-coated paper, can also be used. If the compound is to be imbibed into the support, porous materials such as uncoated paper should be used.

The elements having the described complexes thereon are typically exposed through a pattern of actinic radiation to provide a latent image corresponding to the exposed areas. The transition metal complexes of the present invention are sensitive to actinic radiation such as ultraviolet rays generally in the wavelength range of 1800 to 4000 Angstroms. Many sources of ultraviolet light may be used such as high-pressure mercury vapor lamps, carbon arc lamps, and the like. Some of these complexes are also sensitive to electron-beam exposure, as well as exposure to neutrons and $\alpha$-particles. As used herein, "electromagnetic radiation" is intended to include all of these forms of energy.

In some instances, the rate of development of the described photosensitive element can be considerably accelerated by heating the exposed elements prior to treatment with a physical developer. Thus, a shorter exposure time to achieve a developable image can be used if the element is heated after exposure and prior to development. In some cases, exposed photosensitive complexes of the present invention will "print out" by the application of heat after imagewise exposure. Generally, the element can be heated to about 100° C. to about 200° C. for about 1 to about 60 seconds to exhibit these effects.

After imagewise exposure, an element having a layer containing a complex of the present invention has an imagewise distribution of catalytic transition metal nuclei. By "nuclei" is meant small calalytic specks of elemental metal. This imagewise distribution can be physically developed by contacting the layer with a redox image-forming combination using any of a wide variety of methods. A particularly suitable method is simply to immerse the element into a physical developer bath. Alternatively, the catalyst layer can be overcoated with a viscous physical developer solution. In still another method, the catalyst layer can be contacted with a dry amplification element containing a suitable physical developer composition.

The physical developer composition itself generally contains the reactants for a redox reaction. Either the oxidizing agent or the reducing agent can be the image-forming material. The development can use either the change in electromagnetic radiation absorption or the change in solubility of the image-forming material that takes place as a result of the redox reaction.

A typical physical developer composition contains the salt of a heavy metal ion, a complexing agent for the ion and a reducing agent for the ion. Useful heavy metal salts include silver salts, cupric salts, palladium salts, tellurium salts (including the compounds of the present invention) and nickel salts. The physical developer can also contain a variety of other materials. Useful additives include acids and bases to adjust pH, buffers, preservatives, thickening agents, brighteners, surfactants and the like.

Another type of physical developer produces a dye image. These developers typically contain a reducible dye precursor and a reducing agent. Physically developopable catalysts having deposits of a phthalocyanine or a formazan dye are autocatalytic.

The following references relate to the described and other physical development compositions and processes: U.S. Pat. Nos. 3,223,525, 3,253,923, 3,390,998, 3,576,631, 3,578,449, 3,591,609, 3,650,748, 3,512,972, 3,893,857, 3,935,013, 4,042,392 and 4,046,569; British Pat. No. 1,125,646; *Research Disclosure*, 15631; Hornsby, *Basic Photographic Chemistry* (1956), 66; and Mees and James, *The Theory of the Photographic Process*, 3rd Ed. (1966), pp. 329-331. All of these references are hereby incorporated by reference.

Particularly useful heavy metal physical development baths include the Copper Enplate developer baths (a trademark of Enthone Inc.) containing copper sulfate, formaldehyde, Rochelle salt and nickel sulfate.

Where the element is processed by overcoating the element with the physical developer composition, the overcoat can be any of a wide variety of heat-activatable compositions. These compositions are described, for example, in U.S. Pat. Nos. 3,152,904, 3,330,678 and 3,392,020, British Pat. Nos. 1,110,046, 1,131,108, 1,161,779, 1,342,523 and 1,346,252, and German Pat. No. 888,045, all of which are hereby incorporated by reference. The overcoat can be coated on the element by any means such as those useful for coating the light-sensitive complexes.

The heat-activatable physical developer compositions can comprise a source of silver ion, which is believed to be an oxidizing agent which reacts with a reducing agent, the reaction being catalyzed by the physically developable nuclei. The oxidizing agent, which is preferably a silver salt, should be resistant to darkening under illumination to prevent undesired deterioration of a developed image. Preferably, the silver salt oxidizing agent is a long-chain fatty acid. As employed herein, "long-chain" is intended to mean a chain of carbon atoms containing at least 10 carbon atoms, typically 10-30 carbon atoms. An especially useful class of silver salt oxidizing agents is the silver salt of long-chain fatty acids containing at least 20 carbon atoms. Compounds which are useful silver salts of long-chain fatty acids are, for example, silver behenate, silver stearate, silver oleate, silver laurate, silver hydroxystearate, silver caprate, silver syristate, silver palmitate and the like.

Other silver salt oxidizing agents which are useful in the present invention include silver benzoate, silver phthalate, silver acetate, silver acid phthalate and the like; silver phthalazinone, silver benzotriazole, silver saccharin and the like.

A particularly useful source of silver ion is a dispersion of the silver complex of the ligand 3-carboxy-methyl-4-methyl-4-thiazoline-2-thione. The dispersion of this complex with a reducing agent to form a heat-activatable physical developer composition is described in U.S. Pat. No. 3,785,850 issued Jan. 15, 1974, the disclosure of which is hereby incorporated by reference.

The following examples are presented to illustrate the invention and not to limit it in any way.

EXAMPLE 1: Synthesis of Te{CH$_2$CH$_2$CH$_2$Si(CH$_3$)$_3$]$_2$

Potassium borohydride (44.7 g, 0.828 mole) was added to 700 ml of a 20% aqueous sodium hydroxide solution in a 2-liter, 3-neck flask fitted with a reflux condenser, dropping funnel and argon-gas inlet tube. The solution was deaerated with argon and then tellurium metal (42.2 g, 0.331 g-atom; Alfa Products Tellurium shot, 3.2 mm, m6N) was added. The resulting suspension was refluxed under argon for 2.5 hr to give a clear yellow solution. To this solution of tellurium (2−) was added a deaerated solution of (CH$_3$)$_3$SiCH$_2$CH$_2$CH$_2$Cl (100 g, 0.662 mole) in 800 ml of methanol. The reaction solution was refluxed 20 hr and thereafter the methanol was distilled off. The residual solution was then extracted with two 1-liter ethyl ether portions. The combined ether extracts were washed with water, dried over magnesium sulfate and the ether distilled off to give a pale orange liquid (113 g, 95.6%). The crude telluride was purified by vacuum distillation.

The title compound was confirmed by elemental analysis. Elemental analysis, boiling point and index of refraction for the title compound and other compounds prepared in an analogous manner are presented in Table 1.

TABLE 1

| Compound | Elemental Analysis Calc'd. (Found) | | | bp | n$_D^{20}$ |
| --- | --- | --- | --- | --- | --- |
| | C | H | Te | | |
| Te[CH$_2$Si(CH$_3$)$_3$]$_2$ | 31.81 (28.5) | 7.34 (6.8) | 42.25 (42.3) | 66–68° | 1.5007 |
| Te[CH$_2$Si(CH$_3$)$_2$C$_6$H$_5$]$_2$ | 50.79 (49.3) | 6.15 (6.7) | 29.94 (29.8) | 103–104° | 1.5880 |
| Te[CH$_2$CH$_2$CH$_2$Si(CH$_3$)$_3$]$_2$ | 40.24 (40.0) | 8.44 (8.7) | 35.63 (34.9) | 52° | 1.4988 |

EXAMPLE 2: Synthesis of palladium dichloride complexes with diorganotellurium(II) ligands Method A: PdCl$_2${Te{CH$_2$Si(CH$_3$)$_3$]$_2$}$_2$ To a solution of 3.2 g (10 mmoles) PdCl$_2$(NCC$_6$H$_5$)$_2$ (prepared as described by M. S. Kharasch et al, *J. Amer. Chem. Soc.*, 60, p. 882 (1938)) in 250 ml of benzene were added 3.2 g (10 mmoles) of Te[CH$_2$Si(CH$_3$)$_3$]$_2$. The reaction solution, after stirring at room temperature for 1 hr, was concentrated to dryness and the residue was recrystallized from 175 ml 4:1 methanol-hexane to give, on cooling to −10° C., a crop of orange needles. The title complex was confirmed by elemental analysis.

Method B: PdCl$_2${Te{CH$_2$CH$_2$CH$_2$Si(CH$_3$)$_3$]$_2$}$_2$

To a solution of 1.6 g (5 mmoles) of K$_2$PdCl$_4$ (prepared as described in Gmelin's *Handbuch der Anorganischen Chemie*, 68, p. 83 (1938)) in 150 ml of water was added a solution of 3.6 g (10 mmoles) Te[CH$_2$CH$_2$CH$_2$Si(CH$_3$)$_3$]$_2$ in 150 of methanol. A red precipitate immediately formed. The reaction solution was stirred at room temperature for 15 min, filtered and the crude product washed well with water, ethanol and air-dried. The product was recrystallized from 4:1 methanol-hexane to give 3.2 g of orange crystals. The title complex was confirmed by elemental analysis. The melting point was 70° C.

Both palladium dichloride complexes described above easily formed 1.0 M solutions in diethyl ether.

EXAMPLE 3: Synthesis of Pd(SCN)$_2${Te{CH$_2$Si(CH$_3$)$_3$]$_2$}$_2$

To a solution of 2.6 g (6 mmoles) of K$_2$Pd(SCN)$_4$ (prepared as described by N. J. DeStefano and J. L. Burmeister, *Syn. Inorg. Metal-Organic Chem.*, 3, p. 313 (1973)) in 400 ml methanol were added 3.6 g (12 mmoles) of Te[CH$_2$Si(CH$_3$)$_3$]$_2$. The reaction solution was stirred 60 min at room temperature and then concentrated to dryness under vacuum. The crude red product was recrystallized from 120 ml 4:1 methanol-hexane to give 4.3 g of bright red crystals. The title complex was confirmed by elemental analysis. The melting point was 143° C.

EXAMPLE 4: Synthesis of CuBr{Te{CH$_2$CH$_2$CH$_2$Si(CH$_3$)$_3$]$_2$}$_2$

To a solution of 11.5 g (32 moles) Te—CH$_2$CH$_2$CH$_2$Si(CH$_3$)$_3$]$_2$, prepared as described in Example 1, in 500 ml trichloromethane were added 2.25 g (15.7 mmoles) of solid CuBr (prepared as described in *Inorg. Synth.*, 2, p. 3 (1946)). The reaction solution was stirred at room temperature for 10 hr and then the solvent was removed under vacuum to give a white residue. The residue was washed with 100 ml methanol at room temperature and then recrystallized from 500 ml hot methanol to give 5 g of pure product as white needles. The title complex was confirmed by elemental analysis. The melting point was 55° C.

EXAMPLE 5: Photosensitivity of PdCl$_2${Te{CH$_2$CH$_2$CH$_2$Si(CH$_3$)$_3$]$_2$}$_2$ A solution of 100 mg of PdCl$_2${Te{CH$_2$CH$_2$CH$_2$Si(CH$_3$)$_3$]$_2$}$_2$ (prepared as described in Example 2-B) in 10 ml dichloromethane was imbibed in paper stock and imagewise-exposed for 60 sec under a high-pressure mercury arc. Immersion of this exposed paper in an aqueous dye physical developer (5% in triphenyltetrazolium chloride and 1% in hydrazine) gave a red negative image of the corresponding formazan dye.

EXAMPLE 6: Photothermographic property of CuBr{Te{CH$_2$CH$_2$CH$_2$Si(CH$_3$)$_3$]$_2$}$_2$ A solution containing 100 mg of the title complex (prepared as described in Example 4) dissolved in 10 ml of dichloromethane was imbibed into paper stock. A 30-sec imagewise exposure of this sensitized paper stock under a 360-watt high-pressure mercury arc resulted in a faint yellow printout. Subsequent heating of the exposed paper for 10 sec at 175° C. produced a grey-black negative image.

EXAMPLE 7: The use of CuBr{Te{CH$_2$CH$_2$CH$_2$Si(CH$_3$)$_3$]$_2$}$_2$ as an oxidant in dry physical development A dry element was prepared by dissolving 100 mg of CuBr{Te{CH$_2$CH$_2$CH$_2$Si(CH$_3$)$_3$]$_2$}$_2$ (as an oxidant) and 120 mg of 2,6-dichloro-4-benzenesulfonamidophenol (as a reducing agent) in 10 ml of a 7% solution of poly(vinyl butyral) in a 1:1 solution of acetone and toluene. The resulting image-forming combination was coated at 10 mils wet thickness onto a subbed poly(ethylene terephthalate) support to form an amplification element. This element was laminated to a second piece of poly(ethylene terephthalate) on which a step tablet distribution of nuclei of palladium had been vacuum-evaporated so that the image-forming combination was in contact with the palladium. Passing of the laminate through heated rollers at 175° C. resulted in selective copper amplification of the palladium nuclei down to a coverage of $3.94 \times 10^{-14}$ atoms/cm$^2$.

The invention has been described in detail with particular reference to preferred embodiments thereof, but it will be understood that variations and modifications can be effected within the spirit and scope of the invention.

I claim:

1. A tellurium(II) compound represented by the formula:

Te[(CH$_2$)$_n$SiRR'R'']$_2$ wherein:
n is an integer from 1 to 10 and
R, R' and R'' are independently selected from the group consisting of alkyl, aryl and heterocyclic radicals.

2. A tellurium(II) compound according to claim 1 wherein n is an integer from 1 to 4.

3. A tellurium(II) compound according to claim 1 wherein at least two of R, R' and R'' are lower alkyl.

4. A tellurium(II) compound according to claim 1 wherein n is 1 and R, R' and R'' are methyl.

5. A tellurium(II) compound selected from the group consisting of:

Te[CH$_2$Si(CH$_3$)$_3$]$_2$,

Te[CH$_2$CH$_2$CH$_2$Si(CH$_3$)]$_2$ and

Te[CH$_2$Si(CH$_3$)$_2$C$_6$H$_5$]$_2$.

6. A method of making a tellurium(II) compound represented by the formula:

Te[(CH$_2$)$_n$SiRR'R'']$_2$ wherein:
n is an integer from 1 to 10 and
R, R' and R'' are independently selected from the group consisting of alkyl, aryl and heterocyclic radicals, said method comprising the steps of:
(a) reducing elemental tellurium to tellurium (2−) with a reducing agent and
(b) reacting said tellurium (2−) with silicon-containing alkyl halide, wherein said steps are carried out in an inert atmosphere.

* * * * *